(12) United States Patent
Kadykowski et al.

(10) Patent No.: US 10,045,809 B2
(45) Date of Patent: Aug. 14, 2018

(54) ENDOSCOPIC VESSEL HARVESTER WITH BLUNT AND ACTIVE DISSECTION

(71) Applicant: TERUMO CARDIOVASCULAR SYSTEMS CORPORATION, Ann Arbor, MI (US)

(72) Inventors: Randal J. Kadykowski, South Lyon, MI (US); Kevin R. Line, Ann Arbor, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 372 days.

(21) Appl. No.: 15/070,366

(22) Filed: Mar. 15, 2016

(65) Prior Publication Data
US 2017/0035488 A1 Feb. 9, 2017

Related U.S. Application Data

(60) Provisional application No. 62/201,356, filed on Aug. 5, 2015, provisional application No. 62/201,338, filed on Aug. 5, 2015.

(51) Int. Cl.
*A61B 18/08* (2006.01)
*A61B 18/04* (2006.01)
(Continued)

(52) U.S. Cl.
CPC ............ *A61B 18/082* (2013.01); *A61B 18/04* (2013.01); *A61B 17/32* (2013.01);
(Continued)

(58) Field of Classification Search
CPC ..... A61B 1/00; A61B 1/0008; A61B 1/00098; A61B 1/12; A61B 17/00008; A61B 17/285; A61B 17/32; A61B 17/320016; A61B 17/32002; A61B 17/320092; A61B 17/320758; A61B 2017/00013;
(Continued)

(56) References Cited

U.S. PATENT DOCUMENTS

5,013,312 A 5/1991 Parins et al.
5,980,549 A 11/1999 Chin
(Continued)

*Primary Examiner* — Nathan R Price
*Assistant Examiner* — Bradford C Blaise
(74) *Attorney, Agent, or Firm* — Darryl Newell; MacMillan, Sobanski & Todd, LLC (57) ABSTRACT

A vessel dissector for harvesting a target vessel from a donor has a generally cylindrical tip body with a sloping channel formed along a longitudinal side. A channel bottom provides a channel depth that decreases from a distal channel end to a proximal channel end. The tip body has a crescent-shaped forward lip extending distally from the channel. An arcuate collar is slidably disposed in an arcuate recess within the tip body to selectably bridge the channel at the distal end of the channel to form a ring profile with the forward lip. A first ferromagnetic heating element is disposed along a radially outward surface of the forward lip. A second ferromagnetic heating element is disposed on a distal edge of the arcuate collar. The first and second ferromagnetic heating elements are adapted to be energized simultaneously to make a vasiform cut including a pedicle around the target vessel.

6 Claims, 6 Drawing Sheets

(51) Int. Cl.
  *A61B 18/00* (2006.01)
  *A61B 17/00* (2006.01)
  *A61B 17/32* (2006.01)
  *A61B 17/3207* (2006.01)
  *A61B 18/14* (2006.01)

(52) U.S. Cl.
  CPC .. *A61B 17/32002* (2013.01); *A61B 17/320016* (2013.01); *A61B 17/320092* (2013.01); *A61B 17/320758* (2013.01); *A61B 17/320783* (2013.01); *A61B 18/14* (2013.01); *A61B 18/1402* (2013.01); *A61B 2017/00013* (2013.01); *A61B 2017/00969* (2013.01); *A61B 2017/32004* (2013.01); *A61B 2017/320032* (2013.01); *A61B 2017/320082* (2017.08); *A61B 2017/320093* (2017.08); *A61B 2017/320095* (2017.08); *A61B 2018/00184* (2013.01); *A61B 2018/00202* (2013.01); *A61B 2018/00208* (2013.01); *A61B 2018/00404* (2013.01); *A61B 2018/00428* (2013.01); *A61B 2018/00595* (2013.01); *A61B 2018/00601* (2013.01); *A61B 2018/00607* (2013.01); *A61B 2018/00982* (2013.01); *A61B 2018/142* (2013.01); *A61B 2018/1467* (2013.01)

(58) Field of Classification Search
  CPC .. A61B 2017/00969; A61B 2017/0034; A61B 2017/320024; A61B 2017/320028; A61B 2017/320032; A61B 2017/320044; A61B 2017/320775; A61B 2017/320068; A61B 2017/320069; A61B 2017/320073; A61B 2017/320074; A61B 2017/320075; A61B 2017/320077; A61B 2017/320082; A61B 2017/320092; A61B 2017/320093; A61B 2017/320095; A61B 18/04; A61B 18/08; A61B 18/082; A61B 18/12; A61B 18/14; A61B 18/1402; A61B 18/18; A61B 2018/00404; A61B 2018/00428; A61B 2018/00595; A61B 2018/00982; A61B 2018/00345; A61B 2018/00386; A61B 2018/0041; A61B 2018/00416; A61B 2018/00422; A61B 2018/00482; A61B 2018/00488; A61B 2018/00494; A61B 2018/00607; A61B 2018/184; A61B 2018/00202; A61B 2018/00208; A61B 2018/143; A61B 2018/1467
  See application file for complete search history.

(56) References Cited

U.S. PATENT DOCUMENTS

| | | |
|---|---|---|
| 6,129,661 A | 10/2000 | Iafrati et al. |
| 6,309,400 B2 | 10/2001 | Beaupre |
| 6,428,539 B1 * | 8/2002 | Baxter ........... A61B 17/320016 606/167 |
| 6,527,771 B1 | 3/2003 | Weadock et al. |
| 7,077,803 B2 | 7/2006 | Kasahara et al. |
| 7,331,971 B2 | 2/2008 | Kasahara et al. |
| 7,534,243 B1 * | 5/2009 | Chin ............... A61B 17/00008 606/41 |
| 7,556,633 B2 | 7/2009 | Lindsay |
| 7,601,125 B1 * | 10/2009 | Kai .................... A61B 10/0266 600/564 |
| 7,909,762 B2 | 3/2011 | Usher et al. |
| 7,942,891 B2 | 5/2011 | Genovesi et al. |
| 7,981,133 B2 | 7/2011 | Chin |
| 8,097,010 B2 | 1/2012 | Kasahara et al. |
| 8,292,879 B2 | 10/2012 | Manwaring et al. |
| 8,372,066 B2 | 2/2013 | Manwaring et al. |
| 8,372,096 B2 | 2/2013 | Kadykowski et al. |
| 8,377,052 B2 | 2/2013 | Manwaring et al. |
| 8,414,569 B2 | 4/2013 | Manwaring et al. |
| 8,419,724 B2 | 4/2013 | Manwaring et al. |
| 8,425,503 B2 | 4/2013 | Manwaring et al. |
| 8,430,870 B2 | 4/2013 | Manwaring et al. |
| 8,430,898 B2 | 4/2013 | Wiener et al. |
| 8,491,578 B2 | 7/2013 | Manwaring et al. |
| 8,512,326 B2 * | 8/2013 | Shadduck ............. A61B 18/18 606/167 |
| 8,523,850 B2 | 9/2013 | Manwaring et al. |
| 8,523,851 B2 | 9/2013 | Manwaring et al. |
| 8,523,852 B2 | 9/2013 | Manwaring et al. |
| 8,617,151 B2 | 12/2013 | Denis et al. |
| 8,858,544 B2 | 10/2014 | McNally et al. |
| 8,915,909 B2 | 12/2014 | Manwaring et al. |
| 8,932,279 B2 | 1/2015 | Stringham et al. |
| 9,078,655 B2 | 7/2015 | Manwaring et al. |
| 2003/0065325 A1 * | 4/2003 | Schulze ............ A61B 18/1482 606/50 |
| 2004/0143279 A1 * | 7/2004 | Genovesi ......... A61B 17/00008 606/167 |
| 2006/0178670 A1 * | 8/2006 | Woloszko .......... A61B 18/1402 606/48 |
| 2006/0276815 A1 * | 12/2006 | Lotti ................ A61B 17/00008 606/159 |
| 2008/0208192 A1 | 8/2008 | Kadykowski et al. |
| 2008/0255407 A1 | 10/2008 | Blakeney et al. |
| 2008/0306335 A1 * | 12/2008 | Lau ................. A61B 17/00008 600/106 |
| 2010/0292533 A1 | 11/2010 | Kasahara et al. |
| 2013/0165746 A1 * | 6/2013 | Chin .................... A61B 17/285 600/36 |
| 2013/0282009 A1 * | 10/2013 | Knodel ............ A61B 17/00008 606/47 |
| 2014/0296847 A1 * | 10/2014 | Chin .................. A61B 17/3205 606/41 |
| 2015/0073207 A1 | 3/2015 | Langford |

\* cited by examiner

ENDOSCOPIC VESSEL HARVESTER WITH BLUNT AND ACTIVE DISSECTION

CROSS REFERENCE TO RELATED APPLICATIONS

This application claims priority to U.S. provisional application 62/201,356, filed on Aug. 5, 2015, entitled "Vessel Dissector/Harvester," and to U.S. provisional application 62/201,338, filed on Aug. 5, 2015, entitled "Vessel Cauterizing Ring," both of which are hereby incorporated by reference in their entirety.

STATEMENT REGARDING FEDERALLY SPONSORED RESEARCH

Not Applicable.

BACKGROUND OF THE INVENTION

The present invention relates in general to harvesting of living vessels for use in grafting, and, more specifically, to a harvesting device for endoscopically removing a vessel and a surrounding pedicle of fat and connective tissue using ferromagnetic heating to cut and cauterize tissue.

Blood vessels are often dissected from one portion of a living body to be implanted in another portion of the body by a surgical procedure, such as in a coronary artery bypass graft (CABG) or other cardiovascular procedure. An artery or vein is "harvested" (i.e., removed) from its natural location in a patient's body and reconnected to provide blood circulation elsewhere in the body. Among the preferred sources for the vessels to be used as the bypass graft are the saphenous vein in the leg and the radial artery in the arm.

Endoscopic surgical procedures for harvesting a section of a blood vessel (e.g., the saphenous vein) subcutaneously have been developed in order to avoid disadvantages and potential complications of harvesting of the blood vessel by exposing the desired vein section externally through a continuous incision along the leg. The continuous incision for exposing the vein and for introducing the surgical instruments to seal and sever adjoining tissue and side branches of the vessel results in a significant healing process and associated risks.

The known minimally-invasive endoscopic techniques employ a small incision for locating the desired vessel and for introducing one or more endoscopic devices into the small incision. For example, typical commercially available products for performing the endoscopic blood vessel harvesting procedure include a number of separate endoscopic devices that are each inserted into the patient. These endoscopic devices include, for example, an insufflation mechanism having plastic tubing to supply air or $CO_2$ to insufflate the subcutaneous area; an endoscope having a camera and light cables in order to visualize both the dissection and harvesting procedures; a dissector mechanism to dissect or separate the vessel from connective tissues in the body (i.e., blunt dissection); and a cutting mechanism to sever and seal any side branches from the vessel and then remove the vessel from the body (i.e., active cutting). In certain instances, the combination of mechanisms can be bulky and cumbersome for the clinician performing the vessel harvesting. Also, in certain instances, these mechanisms require that a relatively large diameter wound and cavity be formed within the patient in order to accommodate all the separate mechanisms.

Existing harvesting devices have required an intricate and physically demanding procedure to isolate a vessel from surrounding tissue and to cut and coagulate side branches. This required a high level of skill and practice for the person performing the harvesting procedure. Even with good expertise, several potential sources of damage to the harvested vessel remain. Harvesting typically requires multiple passes of one or more separate devices resulting in much contact with the vessel, potentially leading to endothelial damage. To create a sufficient working space and to allow visualization for tissue separation and side branch cutting, significant insufflation is often used. The $CO_2$ insufflation gas can lead to tissue acidosis, $CO_2$ embolism, and other complications. The common use of electrocauterization for cutting and coagulating the side branches can result in thermal spreading to the harvested vessel and sometimes also results in side branch stubs that are too short for obtaining a good, leakproof seal. Moreover, the delivery of RF electrical energy is bipolar (i.e., requires separate grounding of tissue) which can be undesirable.

It has been discovered that improved patency can be obtained for a vein graft if some surrounding tissue is left intact around the desired vessel. To address the absence of endoscopic devices capable of maintaining a layer of surrounding tissue (i.e., a pedicle) over the harvested vessel, copending U.S. application Ser. No. 14/021,537, filed Sep. 9, 2013, entitled "Single-Pass Endoscopic Vessel Harvesting" discloses a ring-shaped blade mounted to a sheath and disposed in a plane substantially perpendicular to the longitudinal direction and proximal of a dissector tip. The blade forms a lateral loop to encircle the vessel from the flanking tunnel and to make a vasiform cut including a pedicle around the vessel as the sheath advances. The disclosure of application Ser. No. 14/021,537 is incorporated herein by reference.

To reduce some disadvantages that may be associated with electrocauterization or other cutting methods, ferromagnetic heating can be used on a cutting surface to generate a controlled heating, as shown in co-pending U.S. application Ser. No. 14/926,305, filed Oct. 29, 2015, entitled "Single-Pass Endoscopic Vessel Harvesting" which is also incorporated herein by reference. Appropriate ferromagnetic materials and the generation of energizing signals can be as disclosed in U.S. Pat. No. 8,292,879.

SUMMARY OF THE INVENTION

A dissector device of the invention uses a ferromagnetic cutting ring adapted to smoothly cut a vasiform pedicle surrounding a target vessel as well as efficaciously sealing its side branches. The device is adapted to be easily positioned at a starting position over a target vessel to begin the dissection and to guide the dissected tissue away from the device as the dissection proceeds, without requiring a large working space within the body of the patient. A leading edge forming a partial ring guides the target vessel and surrounding fat/connective tissue onto a hot ring of ferromagnetic material, wherein the leading edge acts as a mini-dissector working in concert with the thermal cutting and cauterization provided by the hot ring.

In one aspect of the invention, a vessel dissector is provided for harvesting a target vessel from a donor site. A tubular member extends longitudinally between proximal and distal ends. A generally cylindrical tip body has a sloping channel formed along a longitudinal side of the tip body. A sloping channel bottom provides a channel depth that decreases from a distal end to a proximal end of the channel. The tip body has a crescent-shaped forward lip extending distally from the distal end of the channel. An arcuate collar is slidably disposed in an arcuate recess within the tip body to selectably bridge the channel at the distal end of the channel to form a ring profile with the forward lip. A first ferromagnetic heating element is disposed along a radially outward surface of the forward lip, wherein the first ferromagnetic heating element is spaced from a distal edge of the forward lip. A second ferromagnetic heating element is disposed on a distal edge of the arcuate collar. The first and second ferromagnetic heating elements are adapted to be energized simultaneously to make a vasiform cut including a pedicle around the target vessel, wherein a cut vessel and pedicle are guided through the sloping channel after being cut.

DETAILED DESCRIPTION OF PREFERRED EMBODIMENTS

Figure 1:
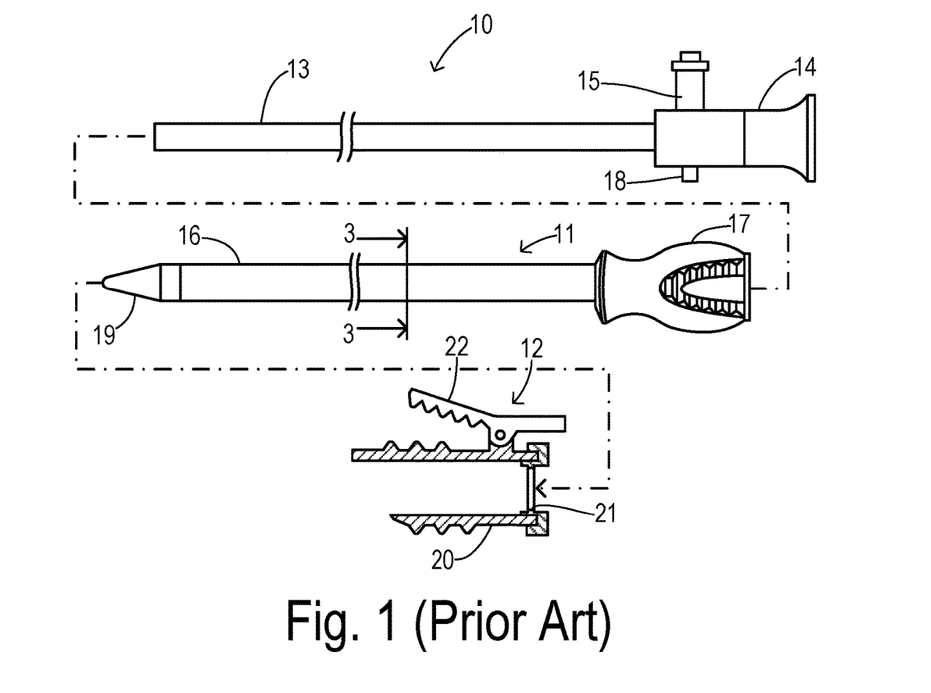
FIG. 1 is a plan view of a prior art blunt dissector with an endoscope and a trocar.

A vessel harvesting system shown in FIG. 1 includes an endoscope 10 to perform observation in a body, a dissector apparatus 11 to dissect a blood vessel in the body, and a trocar 12 to help insert the endoscope 10 and dissector apparatus 11 into the body. Endoscope 10 is a rigid endoscope and includes an elongated rod-like inserting portion 13. The proximal end of inserting portion 13 connects to an end adapter 14 to transmit an endoscopic image. A light guide port 15 projects from end adapter 14. Light guide port 15 connects to a light guide cable to supply illumination light to the endoscope 10.

Dissector apparatus 11 includes a tubular main body portion 16 comprising a hollow longitudinal rod within which endoscope 10 is to be inserted. Endoscope 10 is inserted or removed from longitudinal rod 16 through a handle portion 17. Endoscope 10 may be secured inside dissector 11 by a small nub 18, found opposite light guide port 15 on end adapter 14 of endoscope 10 and held by a conventional mechanism found inside handle portion 17.

The material of longitudinal rod 16 material is selected from fluoropolymers, which are well known materials. Examples of fluoropolymers include polymers such as polytetrafluoroethylene (PTFE commonly referred to as Teflon), perfluoroalkoxy (PFA), fluorinated ethylene propylene (FEP), polyvinylidene fluoride (PVDF), ethylene-tetrafluoroethylene (ETFE), ethylene-chlorotrifluoroethylene (ECTFE), and mixtures of fluoropolymers such as MFA or THV, or mixtures of any of the foregoing. The most preferred material for constituting the outer surface of longitudinal rod 16 is PTFE. The use of a fluoropolymer reduces the friction caused by moving rod 16 through connective tissue, thereby reducing the force required to perform a dissection.

A blunt dissector tip 19 is disposed at the distal end of longitudinal rod 16. Tip 19 has a conical shape and comprises a transparent synthetic resin material to facilitate viewing through tip 19 using endoscope 10. Trocar 12 includes a body 20 to guide dissector apparatus 11 into the incision site. An aperture seal 21 is located on the surface of the proximal end of body 20. Aperture seal 21 allows dissector 11 to be inserted in body 20 of trocar 12 in one fluid forward motion. The outer surface of trocar body 20 includes a projection to engage with living tissue and a holding portion 22 to hold the body 20 onto the living tissue.

To conduct the harvesting of a vessel, an incision may be made in the vicinity of a knee or a wrist immediately above a target blood vessel to be harvested. Body 20 of trocar 12 is inserted in the incision and held by holding portion 22 with respect to the incision. Endoscope 10 is inserted in dissector apparatus 11. Light guide connector 15 of endoscope 10 is inserted in dissector 11. Small nub 18 located on the bottom portion of endoscope 10 engages a mechanism in handle 17 to lock them. The distal end of endoscope 10 is caused to project from the distal end of longitudinal rod 16 into tip 18 for providing a view through tip 18. Endoscope 10 and dissector 11 are then inserted into the body through trocar 12 in one forward movement.

Figure 2:
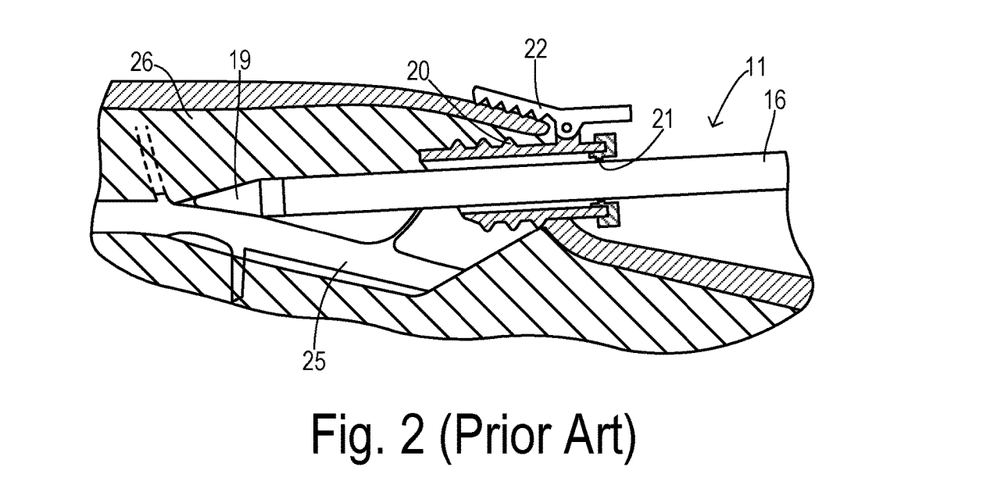
FIG. 2 is a partial cross section showing a dissector inserted into a patient's body and guided by a trocar.

FIG. 2 shows dissector 11 inserted in the body to dissects a portion of a target vessel 25 from connective tissue 26. Blunt tip 19 is adapted to penetrate connective tissue to open a space at or around vessel 25, for example. However, tip 19 in this conventional device is not adapted to create a vasiform cut, to dissect a pedicle surrounding vessel 25, or to otherwise cut or cauterize vessel 25 or any of its side branches.

Figure 3:
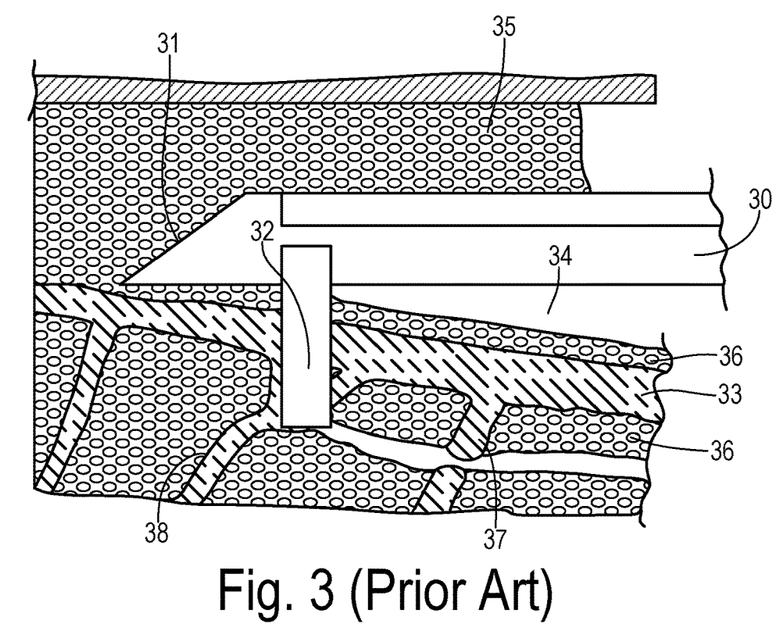
FIG. 3 is a longitudinal cross section showing the active harvesting of a vessel with a surrounding pedicle using an active ring to make a vasiform cut.

FIG. 3 shows a side view of a vessel dissector 30 during the formation of a vasiform cut around a target vessel 33. Dissector 30 includes a blunt tip 31 and a ring blade 32, wherein tip 31 penetrates tissue spaced away from vessel 33 to form a flanking tunnel 34. As an operator advances tip 31 above target vessel 33 so as to maintain an amount of connective tissue 35 between tip 31 and vessel 33, ring blade 32 is energized in order to make a vasiform cut which simultaneously excises pedicle 36 and vessel 33 while automatically severing and cauterizing side branches such as branches 37 and 38. Preferably, ring blade 32 is comprised of a conductor forming a loop which is connected to a signal generator (not shown) via a lead-in section. To provide induction heating for cutting and cauterizing at its edge, appropriate regions of ring blade 32 are coated with a ferromagnetic material (e.g., an alloy coating applied circumferentially over a section of the wire along one of its passes within the loop).

Figure 4:
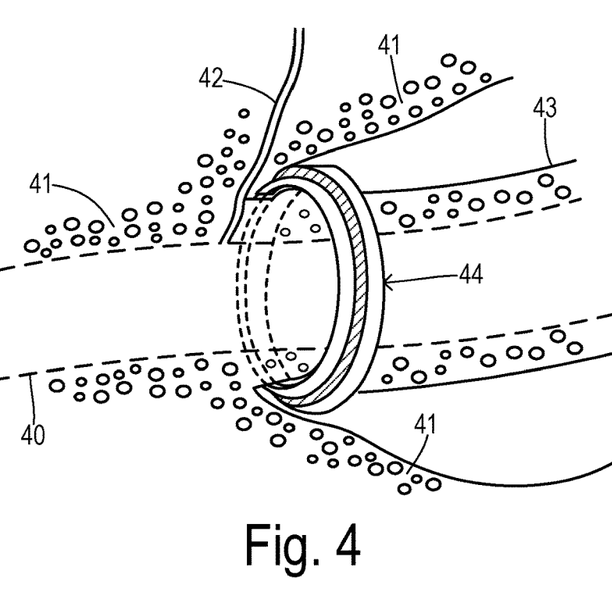
FIG. 4 is a side view of a ring-shaped cutting element comprising a blunt wedge and ferromagnetic heating element to efficaciously cut a target vessel and surrounding pedicle.
Figure 5:
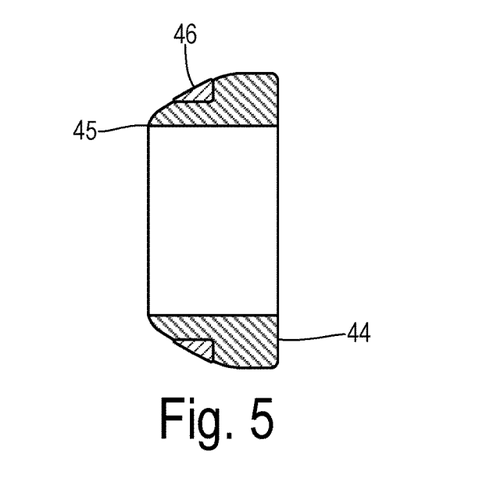
FIG. 5 is a cross-sectional view of the cutting element of FIG. 4.

FIG. 4 depicts a dissecting action which is employed in the present invention. A target vessel 40 surrounded by fat and connective tissue 41 has a side branch 42. To dissect a pedicle 43 having vessel 40 embedded at its center, a dissecting ring 44 is advanced over pedicle 43 in a manner that cuts and cauterizes tissue 41 and side branch 42. Ring 44 would be mounted to the end of a sheath (not shown) or other device for manipulating ring 44. Ring 44 has a generally toroidal shape with a forward lip 45 (FIG. 5) with a blunt wedge shape for providing i) mechanical dissection and ii) deflection and compression of tissue toward a ferromagnetic heating ring 46 disposed on an outer surface of ring 44 spaced proximally back by a short distance (e.g., about 1 mm) from the forward edge of lip 45. As ring 44 advances into tissue 41, the tapered forward edge of lip 45 compresses and guides tissue radially outward along a sloping side of lip 45 in order to become compressed against ferromagnetic heating ring 46, resulting in effective cauterization and creation of a vasiform cut around target vessel 40 and surrounding pedicle 43.

Figure 6:
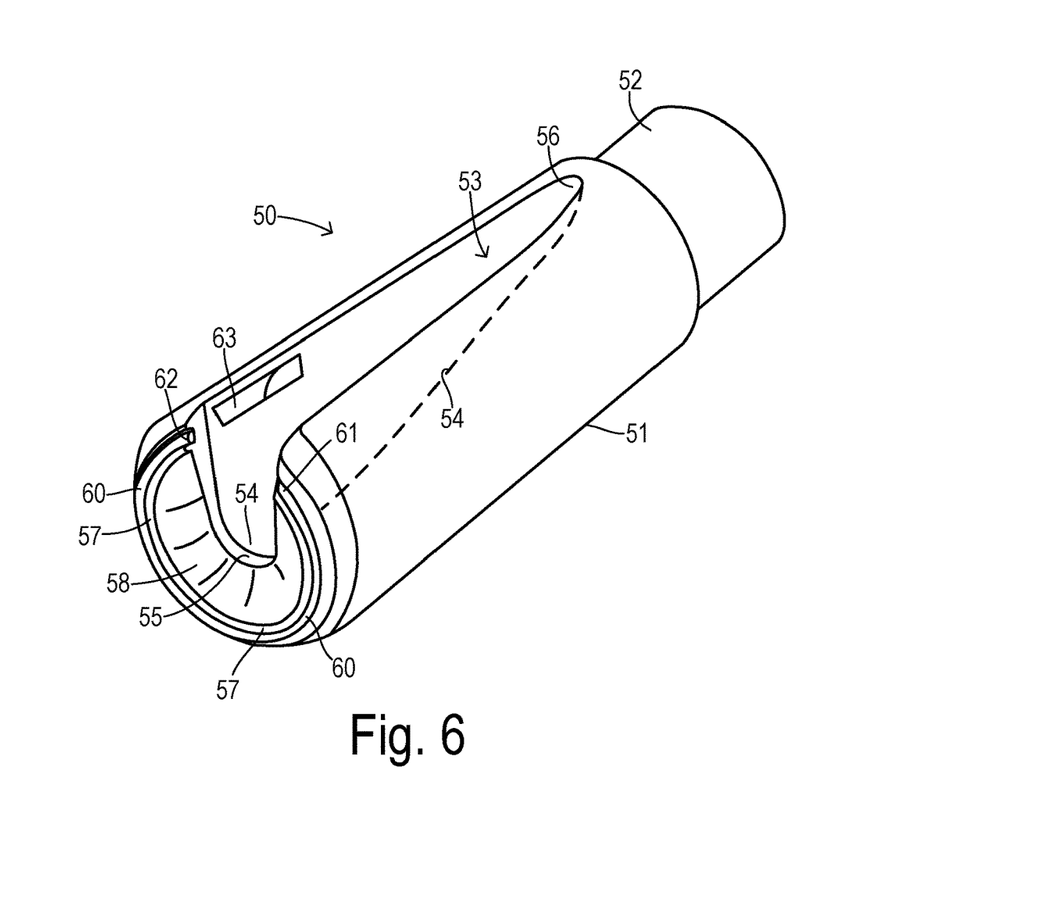
FIG. 6 is a front perspective view of a tip body of a dissector according to a first embodiment with the arcuate collar in an open position.

FIG. 6 shows one preferred embodiment of the invention wherein a vessel dissector 50 includes a generally cylindrical tip body 51 mounted to a distal end of a tubular member (i.e., sheath) 52 having a handle on its proximal end (not shown). Tip body 51 has a sloping channel 53 formed as a curved depression along a longitudinal side of body 51. Channel 53 has a channel bottom 54 which has a channel depth which decreases from a maximum depth at a distal end 55 to a zero depth at a proximal end 56 in order to smoothly guide a dissected pedicle to the side of tubular member 52 as the device advances inside the donor site (e.g., as it moves subcutaneously to harvest a saphenous vein or a radial or mammary artery).

Tip body 51 has a crescent-shaped forward lip 57 providing a blunt tapered wedge at the farthest distal end of tip body 51. A conical ramp surface 58 may be provided between lip 57 and channel 53 to improve tissue compression and to guide newly formed pedicle into channel 53. A ferromagnetic heating element 60 is disposed along an outer surface of the wedge that forms forward lip 57. Element 60 is part of a wire loop extending through tip body 51 and tubular member 52 to a manually-controlled signal generator for energizing ferromagnetic heating element 60 as known in the art. Preferably, the wire loop for element 60 begins at a first end 61, traverses to a second end 62, and then reverses course to returning to first end 61, from which point the wires continue internally through body 51 and member 52 to the signal generator. A ferromagnetic alloy or other ferromagnetic coating is applied only over one or both of the runs between ends 61 and 62.

Figure 7:
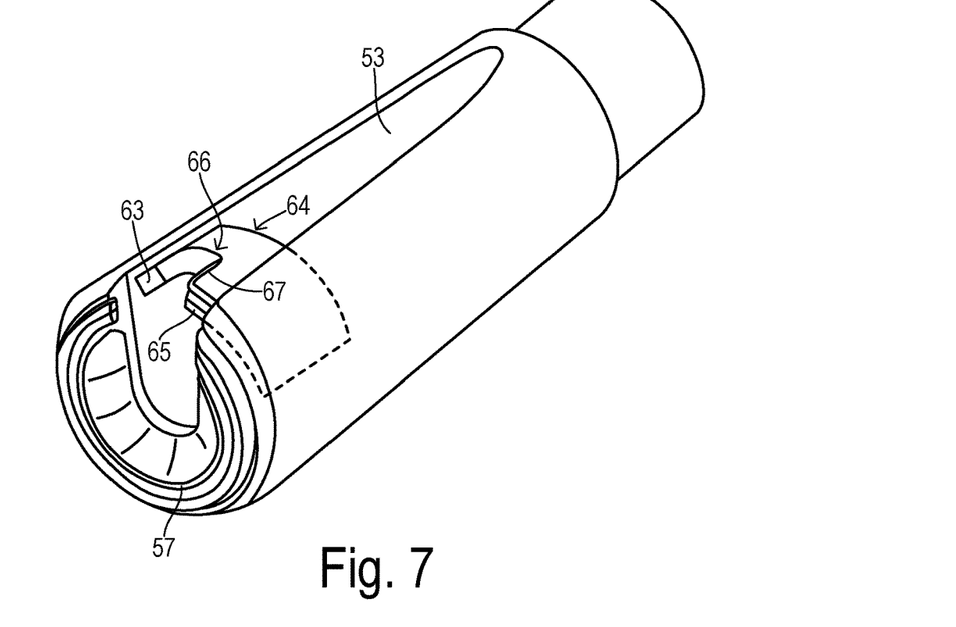
FIG. 7 is a front perspective view of the tip body of FIG. 6 with the arcuate collar in a partially closed position.
Figure 8:
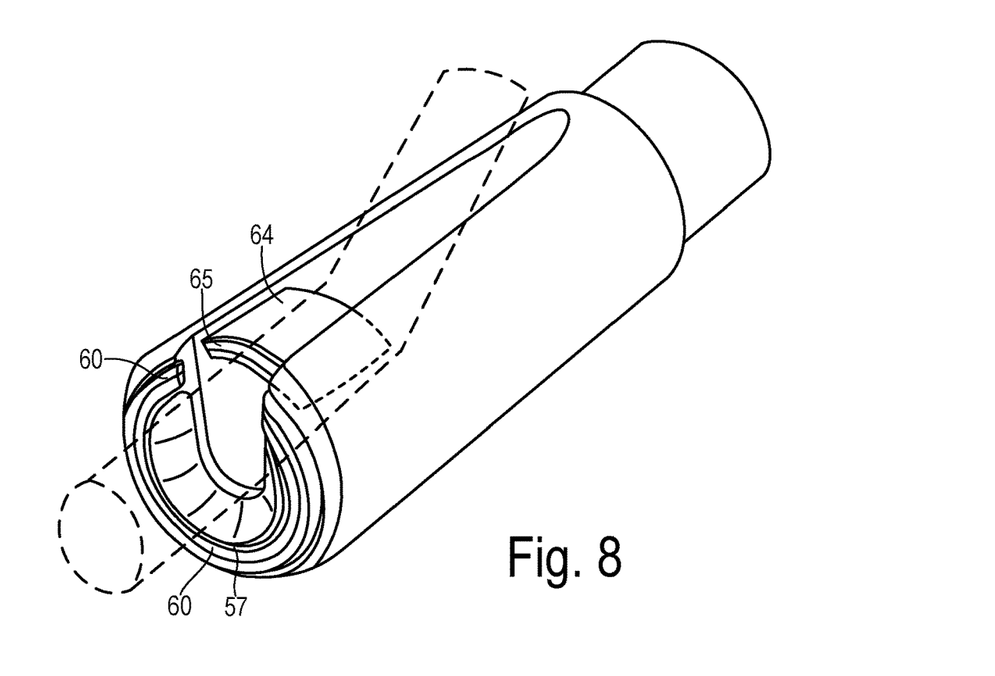
FIG. 8 is a front perspective view of the tip body of FIG. 6 with the arcuate collar in a closed position.

As shown in FIG. 6, body 51 includes an arcuate recess 63 forming at least a partial ring and extending into body 51 from opposed sides of channel 53 as a receptacle for an arcuate collar 64 as shown in FIG. 7. Collar 64 is slidable within recess 63 in order to selectably bridge channel 53 at the distal end of channel 53. When extended to bridge the top of channel 53, collar 64 and lip 57 form a ring profile. A second ferromagnetic heating element 65 is disposed on a forward distal edge of collar 64 so that when channel 53 is being bridged, ferromagnetic heating elements 60 and 65 provided a continuous ferromagnetic cutting surface over a full 360° ring profile to dissect a pedicle, as shown in FIG. 8 with the pedicle being guided to the side of the device after cutting. Arcuate collar 64 may be coupled to a conventional control mechanism for rotating movable elements within an endoscopic vessel dissector (see, e.g., U.S. Pat. No. 7,331, 971 for a mechanism for manually adjusting a position of an endoscopic lens wiping system).

As shown in FIG. 7, arcuate collar 64 may include a step 66 formed along a lateral edge 67 extending transversely from the forward distal edge. Ferromagnetic heating element 65 has a corresponding extension over lateral edge 67 as an additional cutting/cauterizing surface. For example, the extension is useful for cauterizing side branches of the target vessel and for cutting other connective tissues either before, during, or after forming a pedicle. Thus, with arcuate collar 64 initially in an open or partially open condition in which lateral edge 67 is spaced away from the opposite surface of channel 53, a side branch or other tissue can be maneuvered into the space and then collar 64 is rotated toward its closed position to compress the side branch or tissue between the extension of heating element 65 on lateral edge 67 and a surface of sloping channel 53 (e.g., the surface adjacent to the opening of recess 63). When ferromagnetic heating element 65 is energized, the compressed tissue is cut and cauterized.

FIGS. 9-13 show another preferred embodiment of a dissector 70 with a tip body 71 mounted to a dissector rod 72. A distal end of an endoscope unit 73 is shown mounted in an endoscope channel 74 to protrude into sloping channel 75.

Figure 9:
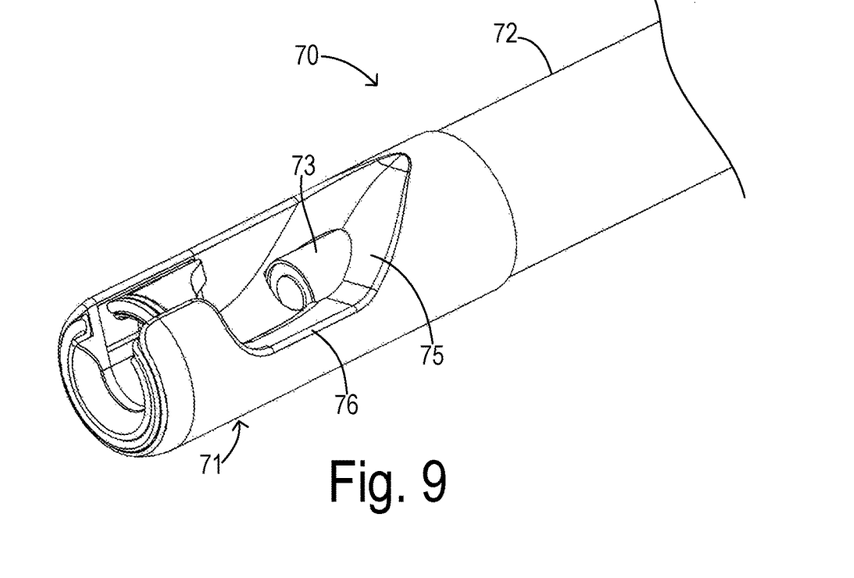
FIGS. 9-11 are front perspective views of a tip body according to a second embodiment, with an arcuate collar in a closed position.
Figure 10:
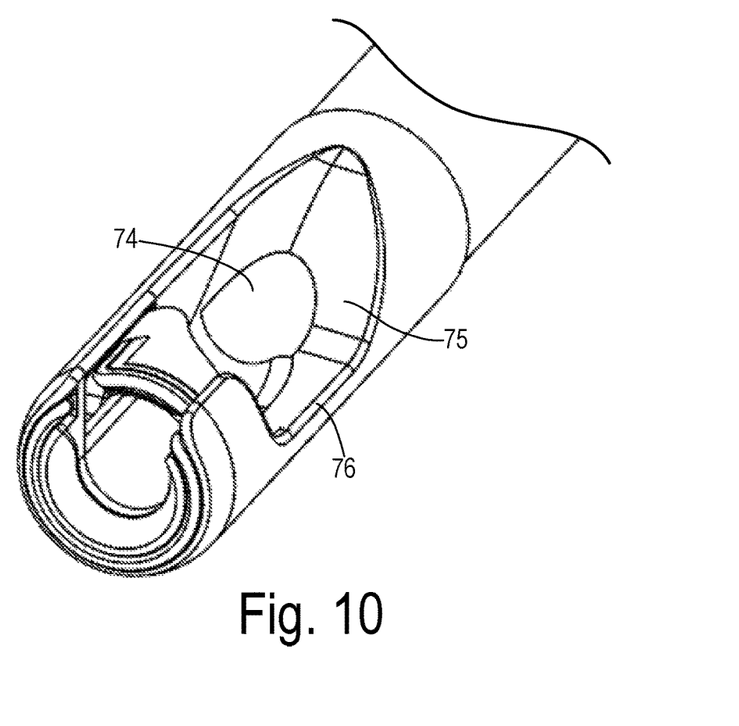
Figure 11:
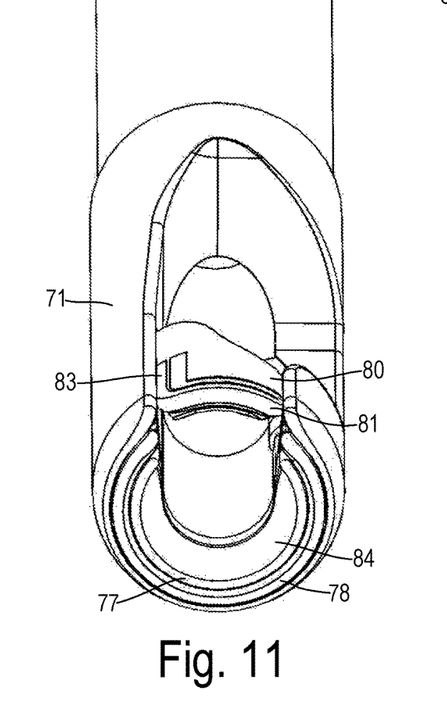

Endoscope 73 is slightly offset from the central longitudinal axis of tip 71. Channel 75 is opened at one side by a side notch 76 so that a pedicle being dissected is guided out from channel 75 away from the offset location of endoscope 73. This opens up a clear viewing area for endoscope 73

Figure 12:
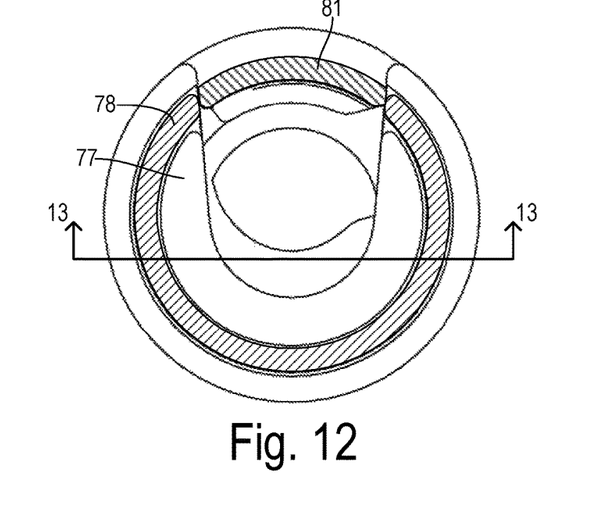
FIG. 12 is an end view of the distal end of the tip body of FIG. 11.

As best shown in FIGS. 11 and 12, body 71 includes forward lip 77 and ferromagnetic heating element 78 forming a partial ring for cutting and cauterizing a pedicle. For cutting in a complete ring to dissect a pedicle, a slidable arcuate collar 80 has a second ferromagnetic heating element 81. Collar 80 is manually rotatable for selectably bridging a gap between the ends of heating element 78 across channel 75, which provides a full cutting ring as seen in FIG. 12. A ramp 84 gently guides a resulting pedicle from a forward lip 77 into channel 75. As in the previous embodiment, ferromagnetic heating element 81 has a lateral extension 83 to provide for the cutting and cauterizing of side branches under compression between extension 83 and a side of channel 75.

Figure 13:
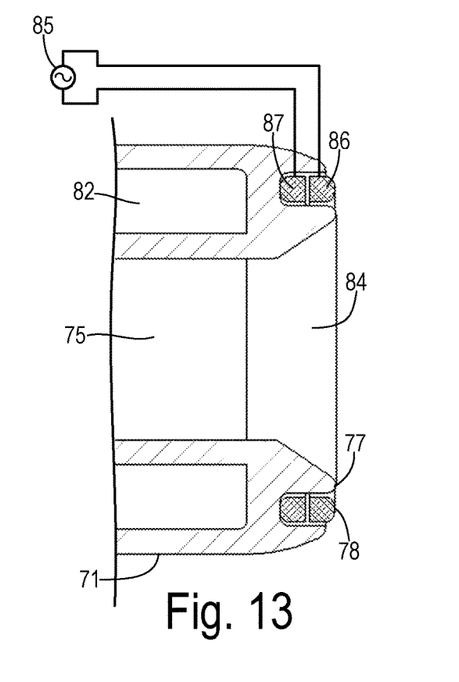
FIG. 13 is a horizontal cross section of a distal end of the tip body along line 13-13 of FIG. 12.

The cross-section in FIG. 13 shows one preferred looping configuration of ferromagnetic heating element 78. In this embodiment, wire loops 86 and 87 are stacked such that only forward loop 86 is exposed to the tissue to be cut. Therefore, the ferromagnetic alloy or coating only needs to be provided on the wire along loop 86 which will be exposed to tissues. The looped wire of element 78 is electrically connected to a signal generator 85. The cross section shows internal recess 82 which is adapted to slidably receive arcuate collar 80.

What is claimed is:

1. A vessel dissector for harvesting a target vessel from a donor site, comprising:
   a tubular member extending longitudinally between proximal and distal ends;
   a generally cylindrical tip body having a sloping channel formed along a longitudinal side of the tip body, wherein a sloping channel bottom provides a channel depth that decreases from a distal end to a proximal end of the channel, and wherein the tip body has a crescent-shaped forward lip extending distally from the distal end of the channel;
   an arcuate collar slidably disposed in an arcuate recess within the tip body to selectably bridge the channel at the distal end of the channel to form a ring profile with the forward lip;

a first ferromagnetic heating element disposed along a radially outward surface of the forward lip, wherein the first ferromagnetic heating element is spaced from a distal edge of the forward lip; and a second ferromagnetic heating element disposed on a distal edge of the arcuate collar, wherein the first and second ferromagnetic heating elements are adapted to be energized simultaneously to make a vasiform cut including a pedicle around the target vessel, wherein the sloping channel is configured to guide the cut target vessel and pedicle.

2. The vessel dissector of claim 1 wherein the forward lip is shaped as a blunt wedge to compress and guide tissue to the first ferromagnetic heating element.

3. The vessel dissector of claim 1 wherein the arcuate collar has a lateral edge transverse to the distal edge, wherein the second ferromagnetic heating element is further disposed on the lateral edge to cauterize a side branch of the target vessel.

4. The vessel dissector of claim 1 wherein the arcuate collar is configured to compress a side branch of the target vessel between the second ferromagnetic heating element and a surface of the sloping channel.

5. The vessel dissector of claim 1 wherein the first and second ferromagnetic heating elements are comprised of respective looped wires each having a portion covered by a ferromagnetic alloy.

6. The vessel dissector of claim 1 further comprising an endoscope extending through the tubular member to protrude into the sloping channel.

* * * * *